United States Patent [19]

Acker et al.

[11] 4,437,878
[45] Mar. 20, 1984

[54] DIHYDROTHIOPHENECARBOXYLATES AND THEIR USE FOR CONTROLLING UNDERSIRABLE PLANT GROWTH

[75] Inventors: Rolf-Dieter Acker, Leimen; Phillip A. Rossy, Ludwigshafen; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 480,895

[22] Filed: Mar. 31, 1983

[30] Foreign Application Priority Data

Mar. 31, 1982 [DE] Fed. Rep. of Germany ....... 3211851

[51] Int. Cl.³ .................... A01N 43/02; C07D 333/24
[52] U.S. Cl. ........................................... 71/90; 549/69
[58] Field of Search .............................. 71/90; 549/69

[56] References Cited

U.S. PATENT DOCUMENTS

| | | | |
|---|---|---|---|
| 2,453,564 | 11/1948 | Baker | 549/69 |
| 3,823,161 | 7/1974 | Lesser | 549/69 |
| 3,828,001 | 8/1974 | Broad et al. | 260/332.2 C |

Primary Examiner—Alan Siegel
Attorney, Agent, or Firm—Keil & Witherspoon

[57] ABSTRACT

Dihydrothiophenecarboxylates of the formula

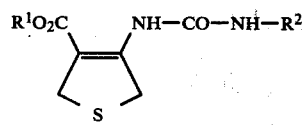

where $R^1$ and $R^2$ have the meanings given in the description, are used for controlling undesirable plant growth.

8 Claims, No Drawings

DIHYDROTHIOPHENECARBOXYLATES AND THEIR USE FOR CONTROLLING UNDESIRABLE PLANT GROWTH

The present invention relates to dihydrothiophenecarboxylates, herbicides containing these compounds as active ingredients, and a method of controlling undesirable plant growth with these active compounds.

It has been disclosed that thiophene derivatives possess herbicidal activity (U.S. Pat. No. 3,828,001).

We have found that dihydrothiophenecarboxylates of the formula $$R^1O_2C\diagdown\qquad NH-CO-NH-R^2 \qquad (I)$$

where $R^1$ and $R^2$ are each $C_1-C_{10}$-alkyl, $C_2-C_{10}$-alkenyl, $C_2-C_{10}$-alkynyl, $C_1-C_{10}$-haloalkyl, $C_2-C_{10}$-alkoxyalkyl, $C_2-C_{10}$-alkylthioalkyl or $C_3-C_7$-cycloalkyl, or are each phenyl which is unsubstituted or substituted by halogen or $C_1-C_4$-alkyl, or are each unsubstituted or halogen-substituted benzyl, and $R^1$ may furthermore be hydrogen, possess herbicidal activity, and are better tolerated by a number of crops than are known thiophenecarboxylates.

In formula I, $R^1$ and $R^2$ are each straight-chain or branched $C_1-C_{10}$-alkyl, preferably $C_1-C_4$-alkyl, straight-chain or branched $C_2-C_{10}$-alkenyl, preferably $C_3-C_4$-alkenyl, straight-chain or branched $C_2-C_{10}$-alkynyl, preferably $C_3-C_4$-alkynyl, straight-chain or branched $C_1-C_{10}$-haloalkyl, preferably $C_1-C_4$-haloalkyl, straight-chain or branched $C_2-C_{10}$-alkoxy- or alkylthioalkyl, preferably $C_2-C_4$-alkoxy- or alkylthioalkyl, or $C_3-C_7$-cycloalkyl, eg. ethyl, n-propyl, isopropyl, n-butyl, isobutyl, sec.-butyl, tert.-butyl, n-pentyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl, tert.-amyl, vinyl, allyl, methallyl, crotyl, 2-ethyl-hexen-2-yl, hexen-5-yl, 2-methylbut-2-enyl, 2-methylbut-1-en-3-yl, but-1-yn-3-yl, but-2-ynyl, but-1-en-3-yl, propargyl, 2-methylbut-2-en-4-yl, 2-methylbut-2-en-4-yl, 3-methylbut-1-en-3-yl, 2-chloroethyl, 2-chloro-n-propyl, 3-chloro-n-propyl, 2-chloroisopropyl, 1-chloromethyl-n-propyl, 2-chlorobut-3-yl, 2-chloro-2-methyl-n-propyl, 2-fluorobut-3-yl, 2-fluoro-2-methyl-n-propyl, 2-fluoroisopropyl, chloro-tert.-butyl, 2,2,2-trifluoroethyl, methoxyethyl, ethoxyethyl, 3-methoxy-n-propyl, methoxyisopropyl, 3-methoxy-n-butyl, 1-methoxybut-2-yl, ethoxy-tert.-butyl, methoxy-tert.-butyl, 2-methoxybutyl, 4-methoxy-n-butyl, methylmercaptoethyl, ethylmercaptoethyl, 3-methylmercapto-n-propyl, 3-methylmercapto-n-butyl, 1-methylmercaptobut-2-yl, methylmercapto-tert.-butyl, 2-methylmercapto-n-butyl, cyclopropyl, cyclopentyl, cyclohexyl or cycloheptyl.

$R^1$ and $R^2$ may each furthermore be benzyl which is unsubstituted or substituted in the phenyl ring by halogen, such as fluorine, chlorine, bromine or iodine, eg. benzyl, 2,6-dichlorobenzyl, 2-chloro-6-fluorobenzyl or 2,6-difluorobenzyl, or phenyl which is unsubstituted or substituted by halogen, such as fluorine, chlorine, bromine or iodine, or by $C_1-C_4$-alkyl, eg. phenyl, 4-chlorophenyl, 2,4-dichlorophenyl, 4-isopropylphenyl or 4-tert.-butylphenyl.

Preferred compounds of the formula I are those in which $R^1$ and $R^2$ are each $C_1-C_4$-alkyl.

The dihydrothiophenecarboxylates of the formula I are obtained by a process wherein (a) a ketoester of the formula $$\underset{S}{\overset{O}{\diagdown}}\quad CO_2R^1 \qquad (II)$$

where $R^1$ has the above meanings, is reacted with a urea of the formula $$R^2-NH-\overset{O}{\underset{\|}{C}}-NH_2 \qquad (III)$$

where $R^2$ has the above meanings, or (b) an amino compound of the formula $$H_2N\diagdown\qquad CO_2R_1 \qquad (IV)$$

where $R^1$ has the above meanings, or a salt of this compound, is reacted with an isocyanate of the formula $$R^2-NCO \qquad (V)$$

where $R^2$ has the above meanings.

Embodiment (a) is carried out at from 0° to 150° C., preferably from 50° to 120° C., with or without the addition of an inert organic solvent. Advantageously, a condensing agent, eg. p-toluenesulfonic acid, phosphoric acid, polyphosphoric acid or sulfuric acid, is added to the reaction mixture, the amount of this agent being from 0.1 to 20 mole %, based on compound II.

To increase the yield, the water formed may be distilled off azeotropically. Compound II can be employed in an amount of from 25 mole % below the stoichiometric amount to 25 mole % above the stoichiometric amount, the percentages being based on compound III.

Ketoesters of the formula II where $R^1$ is methyl are known (J. Org. Chem. 45 (1980), 617). Ketoesters of the formula II where $R^1$ has the meanings given for formula I with the exception of methyl and hydrogen are obtained by transesterification of a $C_1-C_3$-alkyl ester of the formula II with the hydroxy compound of the formula $R^1OH$, where $R^1$ has the meanings given for formula I with the exception of methyl and hydrogen.

In this reaction, it is advantageous to add from 0.1 to 20 mole %, based on compound II, of a basic or acidic catalyst.

Examples of suitable acidic catalysts are inorganic acids, eg. hydrochloric acid, sulfuric acid, phosphoric acid and polyphosphoric acid, as well as aromatic carboxylic acids and sulfonic acids, in particular p-toluenesulfonic acid. Suitable basic catalysts are tertiary amines, alkaline earth metal compounds, ammonium compounds and alkali metal compounds, as well as mixtures of these. Zinc compounds can also be used. Examples of such basic catalysts are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, alpha-picoline, beta-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

Further examples of suitable compounds, in addition to the above inorganic bases, are sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethyleneglycolate, sodium propylene-1,2-glycolate, sodium propylene-1,3-glycolate, sodium diethyleneglycolate, sodium triethyleneglycolate, sodium dipropylene-1,2-glycolate, potassium methylate, potassium ethylate, potassium n-propylate, potassium isopropylate, potassium n-butylate, potassium isobutylate, potassium sec.-butylate, potassium tert.-butylate, potassium methyleneglycolate, potassium propylene-1,2-glycolate, potassium propylene-1,3-glycolate, potassium diethyleneglycolate, potassium triethyleneglycolate and potassium dipropylene-1,2-glycolate.

The ketoesters of the formula II where $R^1$ is ethyl are obtained, for example, by the following reaction:

20 parts by weight of methyl 3-keto-1,5-dihydrothiophene-4-carboxylate, 57.8 parts by weight of ethanol and 1 part by weight of p-toluenesulfonic acid are refluxed for 50 hours, and the mixture is then distilled. 17.1 parts by weight of ethyl 3-keto-1,5-dihydrothiophene-4-carboxylate of melting point 106°–109° C./1.3 mbar are obtained.

Embodiment (b) is carried out using about stoichiometric amounts of substances, ie. about 0.8–1.2 moles of compound IV per mole of compound V, in the presence or absence of an inert organic solvent, at from −20° to +50° C. If compound IV is present in the form of a salt, a base may be added. The free amine can then be isolated, or a compound of the formula V can be directly added. The solution is evaporated down, and the compound of the formula I is purified by recrystallization or chromatography.

Suitable bases are the basic catalysts listed for embodiment (a), and suitable acids are the organic acids stated for that embodiment.

Examples of suitable solvents for both processes are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methylether, diethyl ether, ethylene glycol dimethyl ether, tetrahydrofuran, dioxane, thioanisole and beta,beta'-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic, cycloaliphatic and aromatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, octane, toluene, o-, m- and p-xylene and tetralin, esters, eg. ethyl acetate, ethyl acetoacetate and isobutyl acetate, amides, eg. formamide, methylformamide and dimethylformamide, ketones, eg. acetone and methyl ethyl ketone, and mixtures of these solvents. Advantageously, the solvent is used in an amount of from 100 to 2,000, preferably from 200 to 700, % by weight, based on starting material II or IV.

Both processes can be carried out continuously or batchwise, under atmospheric or superatmospheric pressure; for the sake of simplicity, atmospheric pressure is preferred.

EXAMPLE 1

15.1 parts by weight of methyl 3-keto-1,5-dihydrothiophene-4-carboxylate, 14.2 parts by weight of cyclohexylurea and 0.5 part by weight of p-toluenesulfonic acid in 100 parts by weight of xylene were refluxed for 4 hours in an apparatus equipped with a water separator. The mixture was cooled, and the residue was then filtered off under suction and recrystallized from toluene. 20.3 parts by weight of N-cyclohexyl-N'-(3-methoxycarbonyl-2,5-dihydrothien-4-yl)-urea of melting point 154°–155° C. were obtained.

EXAMPLE 2

9.3 parts by weight of 3-amino-4-methoxycarbonyl-1,5-dihydrothiophene hydrochloride, 6.0 parts by weight of triethylamine, 7.4 parts by weight of cyclohexyl isocyanate and 30 parts by weight of acetonitrile were combined, and the mixture was stirred for 3 hours at 25° C. and then evaporated down. The residue was washed with water and recrystallized from toluene. 4.5 parts by weight of N-cyclohexyl-N'-(3-methoxycarbonyl-2,5-dihydrothien-4-yl)-urea of melting point 153°–154° C. were obtained.

EXAMPLE 3

14.4 parts by weight of methyl 3-keto-3,4-dihydrothiophene-4-carboxylate, 16.1 parts by weight of phenylurea and 0.5 part by weight of toluenesulfonic acid in 90 parts by weight of cyclohexane were refluxed for 3 hours, while stirring, in an apparatus equipped with a water separator. The mixture was cooled, and the residue was then filtered off under suction and recrystallized from ethanol. 16.1 parts by weight of N-phenyl-N'-(3-methoxycarbonyl-2,5-dihydrothien-4-yl)-urea of melting point 182°–184° C. were obtained.

For example, the dihydrothiophenecarboxylates of the formula I which are shown below were, or may be, obtained by a similar procedure.

| No. | $R^1$ | $R^2$ | M.p. [°C.] |
|---|---|---|---|
| 1 | $CH_3$ | $CH_3$ | 203–212 |
| 2 | $CH_3$ | $C_2H_5$ | 118–120 |
| 3 | $CH_3$ | $n-C_3H_7$ | 160–161 |
| 4 | $CH_3$ | $i-C_3H_7$ | 123–125 |
| 5 | $CH_3$ | $n-C_4H_9$ | 135–137 |
| 6 | $CH_3$ | $s-C_4H_9$ | 174–176 |
| 7 | $CH_3$ | $t-C_4H_9$ | |
| 8 | $CH_3$ | $n-C_5H_{11}$ | |
| 9 | $CH_3$ | $i-C_5H_{11}$ | |
| 10 | $CH_3$ | cyclohexyl | 154–155 |
| 11 | $CH_3$ | $CH_2CH=CH_2$ | |
| 12 | $CH_3$ | $CH_2C\equiv CH$ | |
| 13 | $CH_3$ | $C_6H_5$ | 168–171 |
| 14 | $CH_3$ | 4-chlorophenyl | 184–187 |
| 15 | $CH_3$ | 3-chlorophenyl | 183–185 |
| 16 | $CH_3$ | $CH_3OCH_2CH_2$ | |
| 17 | $CH_3$ | $CH_3SCH_2CH_2$ | |
| 18 | $CH_3$ | $ClCH_2CH_2$ | 133–137 |
| 19 | $CH_3$ | $CH_3CH(Cl)CH_2$ | 136–139 |
| 20 | $CH_3$ | $(CH_3)_2NCH_2CH_2$ | |
| 21 | H | $CH_3$ | |
| 22 | H | $C_2H_5$ | |
| 23 | H | $n-C_3H_7$ | |
| 24 | H | $i-C_3H_7$ | |
| 25 | H | $n-C_4H_9$ | |
| 26 | H | $i-C_4H_9$ | |
| 27 | $C_2H_5$ | $CH_3$ | 154–157 |
| 28 | $C_2H_5$ | $C_2H_5$ | |
| 29 | $C_2H_5$ | $n-C_3H_7$ | |
| 30 | $C_2H_5$ | $i-C_3H_7$ | |
| 31 | $C_2H_5$ | $n-C_4H_9$ | |
| 32 | $n-C_3H_7$ | $CH_3$ | |
| 33 | $n-C_3H_7$ | $C_2H_5$ | |
| 34 | $n-C_3H_7$ | $C_6H_{11}$ | |
| 35 | $i-C_3H_7$ | $CH_3$ | 154–157 |
| 36 | $i-C_3H_7$ | $C_2H_5$ | |
| 37 | $i-C_3H_7$ | $n-C_3H_7$ | |
| 38 | $i-C_3H_7$ | $i-C_3H_7$ | |
| 39 | $n-C_4H_9$ | $CH_3$ | |
| 40 | $n-C_4H_9$ | $n-C_3H_7$ | |
| 41 | $n-C_4H_9$ | $C_2H_5$ | |
| 42 | cyclohexyl | $CH_3$ | |
| 43 | cyclohexyl | $C_2H_5$ | |
| 44 | phenyl | $CH_3$ | |
| 45 | phenyl | $C_2H_5$ | |
| 46 | phenyl | $i-C_3H_7$ | |
| 47 | phenyl | $n-C_3H_7$ | |
| 48 | 4-chlorophenyl | $CH_3$ | |
| 49 | 3-chlorophenyl | $CH_3$ | |
| 50 | 4-fluorophenyl | $CH_3$ | |
| 51 | 4-isopropylphenyl | $CH_3$ | |
| 52 | $CH_3$ | $s-C_4H_9$ | 143–144 |
| 53 | $CH_3$ | $-CH(C_2H_5)-C_2H_5$ | 190–192 |
| 54 | $CH_3$ | $-CH(CH_3)-CH_2-CH(CH_3)_2$ | 126–129 |

The compounds of the formula I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 5 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the type of soil, the time of the year, the objective to be achieved and the growth stage of the plants, and varies from 0.05 to 5 kg/ha and more, but is preferably from 0.25 to 3.0 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The soybean and rice plants used for postemergence treatment were grown in a peat-enriched substrate to ensure better growth. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were from 0.5 to 1.0 kg of active ingredient per hectare.

The pots were set up in the greenhouse—species from warmer areas at from 20° to 30° C., and species from moderate climates at 15° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were *Arachys hypogaea, Cassia tora, Chenopodium album, Echinochloa crus-galli, Glycine max., Gossypium hirsutum,* Lamium spp., *Malva neglecta, Oryza sativa, Sida spinose, Sinapis alba,* and *Solanum nigrum.*

On preemergence application, for example compound no. 4, at 3.0 kg/ha, had a good herbicidal action, particularly on *Sinapis alba*. On postemergence application, for instance compounds nos. 1, 3 and 5, at 1.0 kg/ha, combated unwanted plants, and were at the same time selective in crop plants. Compound no. 2, at 0.5 kg/ha, combated broadleaved weeds in groundnuts.

In view of the tolerance and the many application methods possible, the compounds according to the invention, or agents containing them, may be used in a large number of crop plants for removing unwanted plant growth.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus spp.* | apple trees |
| *Manihot esculenta* | cassava |
| *Medicago sativa* | alfalfa (lucerne) |
| *Mentha piperita* | peppermint |
| *Musa spp.* | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus spp.* | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. *vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Zea mays* | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A dihydrothiophenecarboxylate of the formula

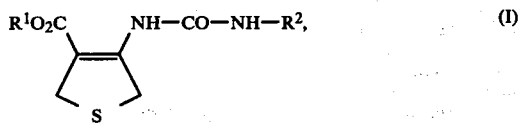

where $R^1$ and $R^2$ are each $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-alkoxyalkyl, $C_2$-$C_{10}$-alkylthioalkyl or $C_3$-$C_7$-cycloalkyl, or are each phenyl which is unsubstituted or substituted by halogen or $C_1$-$C_4$-alkyl, or are each unsubstituted or halogen-substituted benzyl, and $R^1$ may furthermore be hydrogen.

2. A dihydrothiophenecarboxylate of the formula I as claimed in claim 1, where $R^1$ and $R^2$ are $C_1$-$C_4$-alkyl.

3. N-(n-Butyl)-N'-(3-ethoxycarbonyl-2,5-dihydrothien-4-yl)-urea.

4. A herbicide containing inert additives and a dihydrothiophenecarboxylate of the formula I as claimed in claim 1.

5. A herbicide as claimed in claim 4, where $R^1$ and $R^2$ in formula I are $C_1$-$C_4$-alkyl.

6. A herbicide as claimed in claim 4, where the dihydrothiophenecarboxylate is N-(n-butyl)-N'-(3-ethoxycarbonyl-2,5-dihydrothien-4-yl)-urea.

7. A herbicide as claimed in claim 4, containing from 0.1 to 95 wt% of a dihydrothiophenecarboxylate of the formula I.

8. A process for combating the growth of unwanted plants, wherein the unwanted plants and/or the areas to be kept free from unwanted plant growth are treated with a herbicidally effective amount of a dihydrothiophenecarboxylate of the formula I as claimed in claim 1.

* * * * *